US011439411B2

(12) United States Patent
Forstein et al.

(10) Patent No.: US 11,439,411 B2
(45) Date of Patent: Sep. 13, 2022

(54) SYSTEM AND METHOD TO IMPROVE SURGICAL CUTTING IN THE PRESENCE OF SURGICAL DEBRIS

(71) Applicant: THINK Surgical, Inc., Fremont, CA (US)

(72) Inventors: Micah Forstein, Fremont, CA (US); Joel Zuhars, Fremont, CA (US)

(73) Assignee: THINK Surgical, Inc., Fremont, CA (US)

( * ) Notice: Subject to any disclaimer, the term of this patent is extended or adjusted under 35 U.S.C. 154(b) by 199 days.

(21) Appl. No.: 16/880,265

(22) Filed: May 21, 2020

(65) Prior Publication Data

US 2020/0367913 A1   Nov. 26, 2020

Related U.S. Application Data

(60) Provisional application No. 62/852,588, filed on May 24, 2019.

(51) Int. Cl.
*A61B 90/30* (2016.01)
*A61B 17/16* (2006.01)
(Continued)

(52) U.S. Cl.
CPC .......... *A61B 17/1626* (2013.01); *A61B 34/20* (2016.02); *A61B 34/30* (2016.02);
(Continued)

(58) Field of Classification Search
CPC ..... A61B 17/1626; A61B 34/20; A61B 34/30; A61B 90/06; A61B 90/30; A61B 2034/2051; A61B 2034/2055; A61B 2034/2059; A61B 2090/064; A61B 2090/309; A61B 2090/363; A61B 2017/00734; A61B 2217/007
See application file for complete search history.

(56) References Cited

U.S. PATENT DOCUMENTS

5,086,401 A   2/1992   Glassman et al.
6,033,415 A   3/2000   Mittelstadt et al.
(Continued)

*Primary Examiner* — Kevin T Truong
*Assistant Examiner* — Diana Jones
(74) *Attorney, Agent, or Firm* — Pandiscio & Pandiscio (57) ABSTRACT

A system for improved surgical cutting in the presence of surgical debris, the system comprising: a surgical cutter comprising a distal end and a proximal end, the distal end of the surgical cutter being configured to cut bone; a debris detection system mounted to the surgical cutter, the debris detection system comprising: a light source for emitting light; a receiver for receiving light emitted from the light source; and a microprocessor for determining a change in a characteristic of the light emitted by the light source and received by the receiver, and for determining the presence and/or amount of surgical debris present at a surgical site using a change in a characteristic of the light emitted by the light source and received by the receiver; and a controller for varying, based on the presence and/or amount of surgical debris present at the surgical site, at least one of (i) an amount of irrigation supplied to the surgical site, (ii) the feed rate of the surgical cutter, (iii) the direction of the surgical cutter, and (iv) the spindle speed of the surgical cutter.

20 Claims, 6 Drawing Sheets

(51) Int. Cl.
  *A61B 34/30* (2016.01)
  *A61B 90/00* (2016.01)
  *A61B 34/20* (2016.01)
  *A61B 17/00* (2006.01)

(52) U.S. Cl.
  CPC .............. *A61B 90/06* (2016.02); *A61B 90/30* (2016.02); *A61B 2017/00734* (2013.01); *A61B 2034/2051* (2016.02); *A61B 2034/2055* (2016.02); *A61B 2034/2059* (2016.02); *A61B 2090/064* (2016.02); *A61B 2090/309* (2016.02); *A61B 2090/363* (2016.02); *A61B 2217/007* (2013.01)

(56) References Cited

U.S. PATENT DOCUMENTS

| | | |
|---|---|---|
| 6,061,644 A | 5/2000 | Leis |
| 7,206,626 B2 | 4/2007 | Quaid, III |
| 8,010,177 B2 | 8/2011 | Csavoy et al. |
| 8,287,522 B2 | 10/2012 | Moses et al. |
| 8,876,830 B2 | 11/2014 | Hodorek et al. |
| 8,961,536 B2 | 2/2015 | Nikou et al. |
| 10,588,641 B2 * | 3/2020 | Park .................. A61B 17/50 |
| 2007/0085496 A1 * | 4/2007 | Philipp ................ H02P 6/16 318/139 |
| 2008/0009697 A1 * | 1/2008 | Haider .................. G16H 40/63 600/407 |
| 2013/0060278 A1 | 3/2013 | Bozung et al. |
| 2015/0066030 A1 * | 3/2015 | McGinley ............. A61B 17/16 606/79 |
| 2016/0089154 A1 * | 3/2016 | Chien ................ A61B 17/1671 606/79 |
| 2016/0120553 A1 * | 5/2016 | Xie .................... A61B 17/1628 606/80 |
| 2016/0374770 A1 * | 12/2016 | Janik ................... A61B 34/20 604/500 |
| 2017/0000572 A1 * | 1/2017 | Moctezuma de la Barrera ......... A61B 34/20 |
| 2017/0245945 A1 | 8/2017 | Zuhars et al. |
| 2018/0289432 A1 * | 10/2018 | Kostrzewski .......... A61B 34/30 |
| 2018/0317999 A1 * | 11/2018 | Park .................. A61B 18/1445 |
| 2018/0344409 A1 | 12/2018 | Bonny et al. |
| 2019/0365346 A1 * | 12/2019 | Elliot ................... A61B 6/505 |

* cited by examiner

100

102
Detect a presence or amount of surgical debris while cutting a bone at a surgical site, wherein the detection occurs with a light emitter and a receiver positioned on an axis of a cutting tool where an intensity of light detected on the receiver after the light has passed through or reflected from the debris indicates the presence or amount of surgical debris

104
Adjust at least one of an amount of irrigation supplied to the surgical site, a feed rate of the cutting tool, a direction of the cutting tool, and a spindle speed of a cutter based on the detected presence or amount of surgical debris

202
Providing a light source and a receiver positioned on an axis of a cutting tool, said cutting tool configured to remove bone at a surgical site

204
Emitting light from the light source towards the surgical site and detecting the light on the receiver after the light has passed through or reflected from surgical debris present at the surgical site

206
Determining an amount of surgical debris based on an intensity of the light detected by the receiver

208
Adjusting at least one of an amount of irrigation supplied to the surgical site, a feed rate of the cutting tool, a direction of the cutting tool, and a spindle speed of a cutter based on the determined amount of surgical debris

402
Providing a cutting tool, an audio sensor, and a force sensor, said cutting tool configured to cut bone at a surgical site, said audio sensor positioned approximate to the cutting tool to receive cutting audio data, and said force sensor positioned approximate to the cutting tool to sense forces experienced on the cutting tool while cutting bone

404
Collecting, in real-time, cutting audio data from the audio sensor and force data from the force sensor while cutting a bone

406
Determining expected forces on the cutting tool from the audio data

408
Comparing the expected forces to the force data to determine if surgical debris is binding the cutting tool as characterized by the force data being greater than the expected forces

410
Adjusting at least one of an amount of irrigation supplied to the surgical site, a feed rate of the cutting tool, a direction of the cutting tool, and a spindle speed of a cutter if the surgical debris is binding the cutting tool

SYSTEM AND METHOD TO IMPROVE SURGICAL CUTTING IN THE PRESENCE OF SURGICAL DEBRIS

REFERENCE TO PENDING PRIOR PATENT APPLICATION

This patent application claims benefit of U.S. Provisional Patent Application Ser. No. 62/852,588, filed May 24, 2019 by THINK Surgical, Inc. and Micah Forstein et al. for SYSTEM AND METHOD TO IMPROVE SURGICAL CUTTING IN THE PRESENCE OF SURGICAL DEBRIS, which patent application is hereby incorporated herein by reference.

TECHNICAL FIELD

The present invention generally relates to the field of computer-assisted and/or robotic orthopedic surgery, and more particularly to a system and method for improving the performance of a computer-assisted and/or robotic surgical cutting system in the presence of surgical debris.

BACKGROUND

Joint arthroplasty is a surgical procedure to modify an arthritic, degenerated, or damaged joint with artificial components in order to improve the patient's quality of life and mobility. A joint replacement procedure is generally characterized by modifying the affected joint with a series of bone cuts to prepare the joint to precisely receive artificial components, e.g., plates, screws, knee implants, hip implants, shoulder implants, etc. During the process of preparing the affected joint (e.g., during the process of surgical cutting), bone chips, fluids and/or other debris is typically generated at the surgical site. These bone chips, fluids and/or other debris may adversely affect the performance of the computer-assisted and/or robotic surgical cutting system, and may obstruct the view of the anatomy (e.g., the surgical site) and/or pose an increased risk of infection to the patient. Typically, the surgical site is cleared of debris (e.g., bone chips, fluid, etc.) by using an irrigation tube to provide irrigation fluid to the surgical site in concert with a suction device (wielded by a surgeon or technician) that collects the irrigation fluid and/or the debris present at the surgical site. However, with this approach, no data or feedback is collected with respect to the amount of surgical debris or how the surgical debris may affect the cutting performance, which data may otherwise be used to improve the cutting performance of the cutting system (i.e., by taking into account the amount and/or nature of the debris at the surgical site).

Thus there exists a need for a system and method to detect the presence and/or amount of surgical debris present at a surgical site during computer-assisted and/or robotic surgical cutting in order to improve the performance of the cutting system.

SUMMARY OF THE INVENTION

The present invention comprises the provision and use of a novel system and method to detect the presence and/or amount of surgical debris present at a surgical site during computer-assisted and/or robotic surgical cutting in order to improve the performance of the cutting system.

In one preferred form of the invention, there is provided a system for improved surgical cutting in the presence of surgical debris, the system comprising:
a surgical cutter comprising a distal end and a proximal end, the distal end of the surgical cutter being configured to cut bone;
a debris detection system mounted to the surgical cutter, the debris detection system comprising:
a light source for emitting light;
a receiver for receiving light emitted from the light source; and
a microprocessor for determining a change in a characteristic of the light emitted by the light source and received by the receiver, and for determining the presence and/or amount of surgical debris present at a surgical site using a change in a characteristic of the light emitted by the light source and received by the receiver; and
a controller for varying, based on the presence and/or amount of surgical debris present at the surgical site, at least one of (i) an amount of irrigation supplied to the surgical site, (ii) the feed rate of the surgical cutter, (iii) the direction of the surgical cutter, and (iv) the spindle speed of the surgical cutter.

In another preferred form of the invention, there is provided a method for improving surgical cutting in the presence of surgical debris, the method comprising:
providing a system comprising:
a surgical cutter comprising a distal end and a proximal end, the distal end of the surgical cutter being configured to cut bone;
a debris detection system mounted to the surgical cutter, the debris detection system comprising:
a light source for emitting light;
a receiver for receiving light emitted from the light source; and
a microprocessor for determining a change in a characteristic of the light emitted by the light source and received by the receiver, and for determining the presence and/or amount of surgical debris present at a surgical site using a change in a characteristic of the light emitted by the light source and received by the receiver; and
a controller for varying, based on the presence and/or amount of surgical debris present at the surgical site, at least one of (i) an amount of irrigation supplied to the surgical site, (ii) the feed rate of the surgical cutter, (iii) the direction of the surgical cutter, and (iv) the spindle speed of the surgical cutter;
causing the light source to emit light;
causing the receiver to detect light emitted by the light source;
using the microprocessor to determine a change in a characteristic of the light emitted by the light source and received by the receiver, and using the microprocessor to determine the presence and/or amount of surgical debris present at a surgical site using a change in a characteristic of the light emitted by the light source and received by the receiver; and
using the controller to vary, based on the presence and/or amount of surgical debris present at the surgical site, at least one of (i) an amount of irrigation supplied to the surgical site, (ii) the feed rate of the surgical cutter, (iii) the direction of the surgical cutter, and (iv) the spindle speed of the surgical cutter.

In another preferred form of the invention, there is provided a system for improved surgical cutting in the presence of surgical debris, the system comprising:

a surgical cutter comprising a distal end and a proximal end, the distal end of the cutting tool being configured to cut bone;

an audio sensor for collecting audio data emitted during operation of the cutting tool;

a force sensor for collecting force data concerning forces experienced by the cutting tool during operation of the cutting tool;

a microprocessor for determining the expected forces on the surgical cutter tool from the audio data and for comparing the expected forces to the force data to determine if surgical debris is present and binding the surgical cutter at the surgical site; and a controller for varying, based on the presence and/or amount of surgical debris present at the surgical site, at least one of (i) the amount of irrigation supplied to the surgical site, (ii) the feed rate of the surgical cutter, (iii) the direction of the surgical cutter, and (iv) the spindle speed of the surgical cutter.

In another preferred form of the invention, there is provided a method for improved surgical cutting in the presence of surgical debris, the method comprising:

providing a system comprising:
  a surgical cutter comprising a distal end and a proximal end, the distal end of the cutting tool being configured to cut bone;
  an audio sensor for collecting audio data emitted during operation of the cutting tool;
  a force sensor for collecting force data concerning forces experienced by the cutting tool during operation of the cutting tool;
  a microprocessor for determining the expected forces on the surgical cutter tool from the audio data and for comparing the expected forces to the force data to determine if surgical debris is present and binding the surgical cutter at the surgical site; and
  a controller for varying, based on the presence and/or amount of surgical debris present at the surgical site, at least one of (i) the amount of irrigation supplied to the surgical site, (ii) the feed rate of the surgical cutter, (iii) the direction of the surgical cutter, and (iv) the spindle speed of the surgical cutter;

operating the surgical cutter at the surgical site such that the cutting tool engages the surgical site;

collecting audio data from the audio sensor while operating the surgical cutter at the surgical site;

collecting force data from the force sensor while operating the surgical cutter at the surgical site;

using the microprocessor to determine the expected forces on the surgical cutter tool from the audio data, and using the microprocessor to compare the expected forces to the force data to determine if surgical debris is present and binding the surgical cutter at the surgical site; and using the controller to vary, based on the presence and/or amount of surgical debris present at the surgical site, at least one of (i) an amount of irrigation supplied to the surgical site, (ii) the feed rate of the surgical cutter, (iii) the direction of the surgical cutter, and (iv) the spindle speed of the surgical cutter.

BRIEF DESCRIPTION OF THE DRAWINGS

The present invention is further detailed with respect to the following drawings that are intended to show certain aspects of the present of invention, but should not be construed as a limit on the practice of the invention, wherein.

DETAILED DESCRIPTION

The present invention has utility as a system and method to detect the presence and/or amount of surgical debris present at a surgical site during computer-assisted and/or robotic surgical cutting so as to improve the performance of a cutting system. The present invention will now be described with reference to the following embodiments. As is apparent from the following description, and as will be appreciated by those skilled in the art, the present invention can be embodied in different forms and should not be construed as limited to the embodiments set forth herein. For example, features illustrated with respect to one embodiment can be incorporated into other embodiments, and features illustrated with respect to a particular embodiment may be deleted from the embodiment. In addition, numerous variations and additions to the embodiments suggested herein will be apparent to those skilled in the art in light of the instant disclosure. Hence, the following specification is intended to illustrate some particular embodiments of the invention, and not to exhaustively specify all permutations, combinations, and variations thereof.

Furthermore, it should be appreciated that although the systems and methods described herein may make reference to, or show, the proximal femur (e.g., in connection with hip arthroplasty), the systems and methods of the present invention may be applied to other bones and joints in the body, including, but not limited to, other portions of the hip, the ankle, the elbow, the wrist, the skull, the spine, etc. as well as revisions of initial repairs or replacements of any of the aforementioned bones or joints.

As used herein, the term "pre-operative bone data" refers to bone data used to pre-operatively plan a procedure before making modifications to the actual bone. The pre-operative bone data may include one or more of the following: an image data set of a bone (e.g., an image set acquired via computed tomography (CT), magnetic resonance imaging (MRI), ultrasound, x-ray, laser scan, etc.), a virtual generic bone model, a physical bone model, a virtual patient-specific bone model generated from an image data set of a bone, a set of data collected directly on a bone intra-operatively (e.g., as is commonly used with imageless computer-assist devices), etc.

As used herein, the term "registration" refers to the determination of the position and orientation (POSE) and/or coordinate transformation between two or more objects or coordinate systems such as a computer-assist device, a bone, pre-operative bone data, surgical planning data (e.g., an implant model, a computer software "cut-file" to identify a cutting path, virtual boundaries, virtual planes, cutting parameters associated with or defined relative to the pre-operative bone data, etc.), and any external landmarks (e.g., a fiducial marker array, an anatomical landmark, etc.) associated with the bone, if such landmarks exist. Various methods of registration are well known in the art and are described in, for example, U.S. Pat. Nos. 6,033,415; 8,010,177; and 8,287,522, which patents are hereby incorporated herein by reference.

As used herein, the term "real-time" refers to the processing of input data within milliseconds such that calculated values are available within 2 seconds of computational initiation.

As used herein, the term "light source" refers to a device capable of emitting light including infrared, visible, and ultraviolet light. Examples of a light source include a light emitting diode (LED), a laser, or other light emitting device.

As used herein, a "receiver" or "detector" refers to a device capable of detecting the light emitted from the light source, illustratively including a photosensor or camera.

In particular embodiments, the cutting system described herein is a "robotic surgical device". A robotic surgical device refers to any device (or system) requiring computer control of an end-effector to aid in a surgical procedure. Examples of a robotic surgical device include active and haptic, 1 to N degree(s) of freedom (DOF) hand-held surgical devices and systems, autonomous serial-chain manipulator systems, haptic serial chain manipulator systems, parallel robotic systems, master-slave robotic systems, etc., as described in, for example, U.S. Pat. Nos. 5,086,401; 7,206,626; 8,876,830; and 8,961,536; U.S. Pat. App. Pub. No. 2013/0060278; and U.S. patent application Ser. No. 15/778,811, which patents, patent publications and patent applications are hereby incorporated herein by reference. An exemplary embodiment of a robotic surgical system is described below.

Figure 1:
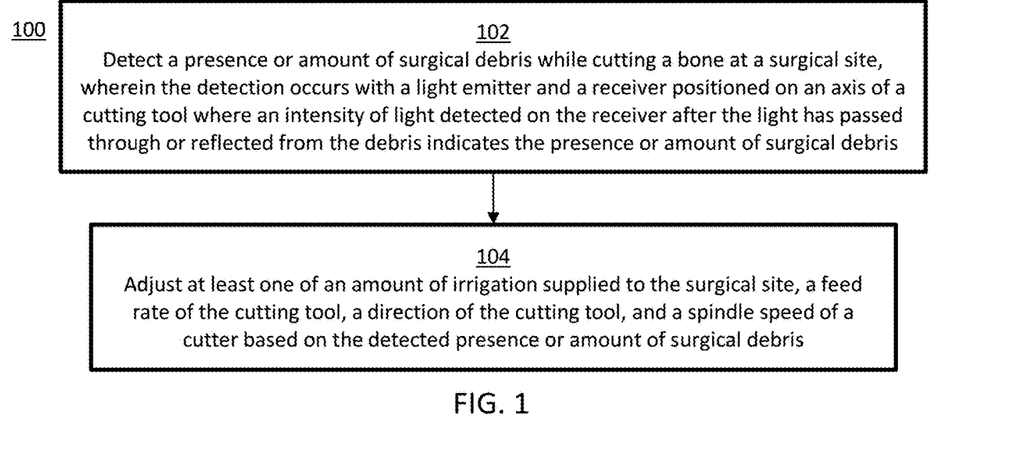
FIG. 1 is a flow diagram showing a novel system and method for detecting the presence and/or amount of surgical debris present at a surgical site during cutting, wherein the novel system uses a light source and a receiver (i.e., a detector) to detect the presence and/or amount of surgical debris present at the surgical site and uses that information to improve the performance of a computer-assisted and/or robotic surgical cutting system.

Method of Detecting Surgical Debris with a Light Source to Improve Cutting Performance With reference now to the drawings, FIG. 1 depicts an embodiment of a method 100 to detect surgical debris at a surgical site using a novel debris detection system comprising a light source and a receiver (i.e., a detector) for detecting light, the data from which may be used to improve the cutting performance of a cutting system as will hereinafter be discussed in further detail.

The method comprises the following steps. The presence and/or amount of surgical debris is detected using the novel debris detection system of the present invention while the computer-assisted and/or robotic surgical is cutting bone at a surgical site. The detection occurs with a light emitter and a receiver (i.e., a detector) positioned on an axis of a cutting tool (e.g., aligned with the longitudinal axis of the cutting tool) where an intensity of light is detected by the receiver after light has passed through, or been reflected by, the debris so as to indicate the presence, or amount, of surgical debris present at the surgical site [see block 102]. Based on the presence and/or amount of surgical debris, the intensity of the light emitted by the light emitter is attenuated by the surgical debris before the emitted light is received by the receiver and, in response to the degree to which the intensity of the emitted light is attenuated by the surgical debris (i.e., in response to how much surgical debris is located at the surgical site), the cutting system adjusts at least one of (i) the amount of irrigation fluid supplied to the surgical site, (ii) the feed rate of the cutting tool, (iii) the direction of the cutting tool, and (iv) the spindle speed of the cutting tool [see block 104].

Figure 2:
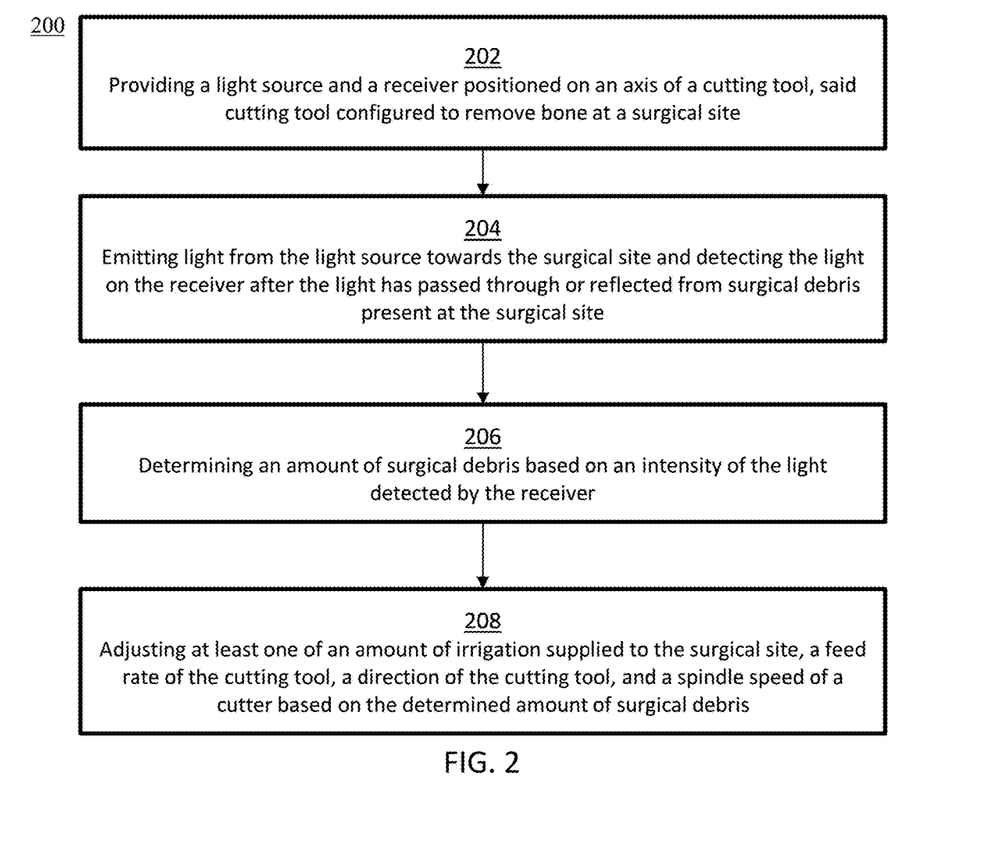
FIG. 2 is a flow diagram showing how the novel system and method of the present invention may be used to determine the amount of surgical debris present at the surgical site during cutting, wherein the novel system uses a light source and a detector to detect the presence and/or amount of surgical debris present at the surgical site and uses that information to improve the performance of a computer-assisted and/or robotic surgical cutting system.

In another form of the invention, and looking now at FIG. 2, the novel debris detection system of the present invention may be used to detect surgical debris at a surgical site using a light source and a receiver (i.e., a detector). Data from the novel debris detection system may then be used to improve the cutting performance of a cutting system. Still looking at FIG. 2, method 200 comprises the following steps. A light source and a receiver positioned on an axis of a cutting tool (e.g., aligned with the longitudinal axis of the cutting tool) is provided, where the cutting tool is configured to cut bone at a surgical site [see block 202]. Light is emitted from the light source towards the surgical site and detected by the receiver after the light has passed through (or been reflected by) any surgical debris present at the surgical site [see block 204]. The amount of surgical debris present at the surgical site is determined based on the intensity of the light detected by the receiver [see block 206]. Based on the determined amount of surgical debris present at the surgical site, the computer-assisted and/or robotic surgical cutting system adjusts at least one of (i) the amount of irrigation supplied to the surgical site, (ii) the feed rate of the cutting tool, (iii) the direction of the cutting tool, and (iv) the spindle speed of the cutting tool.

Additional features of the novel debris detection system of the present invention and/or specific embodiments of the aforementioned methods (100, 200) are further described below.

Figure 3:
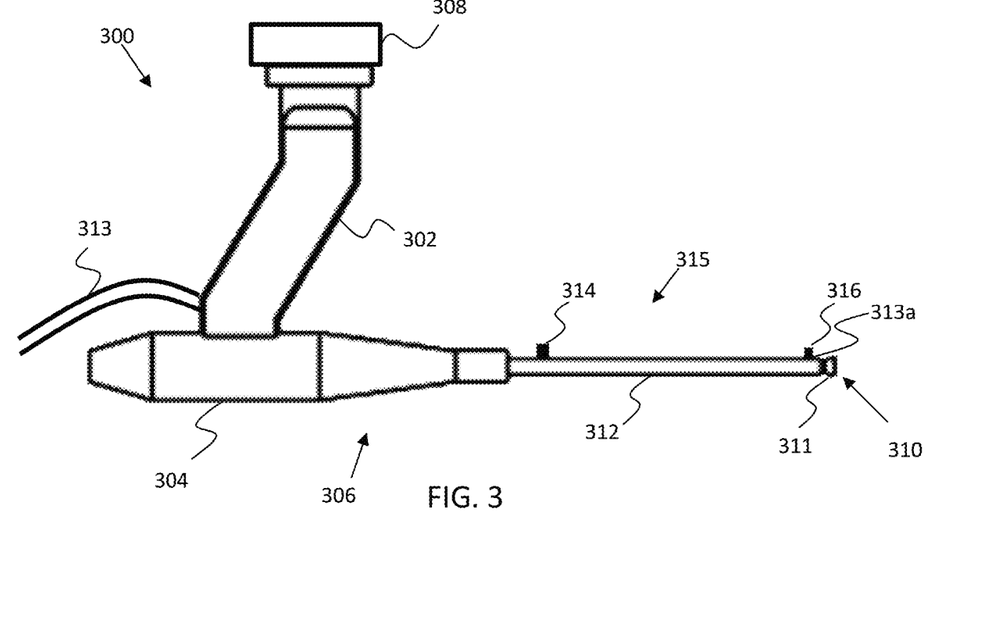
FIG. 3 is a schematic view showing an exemplary end-effector assembly having a cutting tool comprising a novel debris detection system comprising a light source and a receiver (i.e., a detector) formed in accordance with the present invention.
Figure 4:
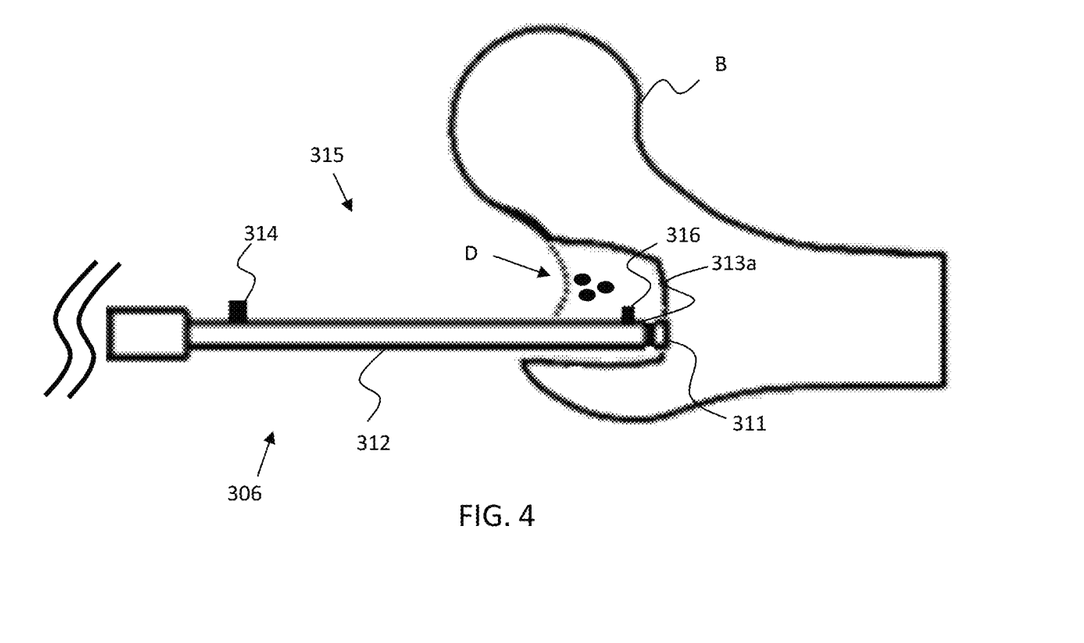
FIG. 4 is a schematic view showing an exemplary cutting tool removing bone in the presence of surgical debris.
Figure 5:
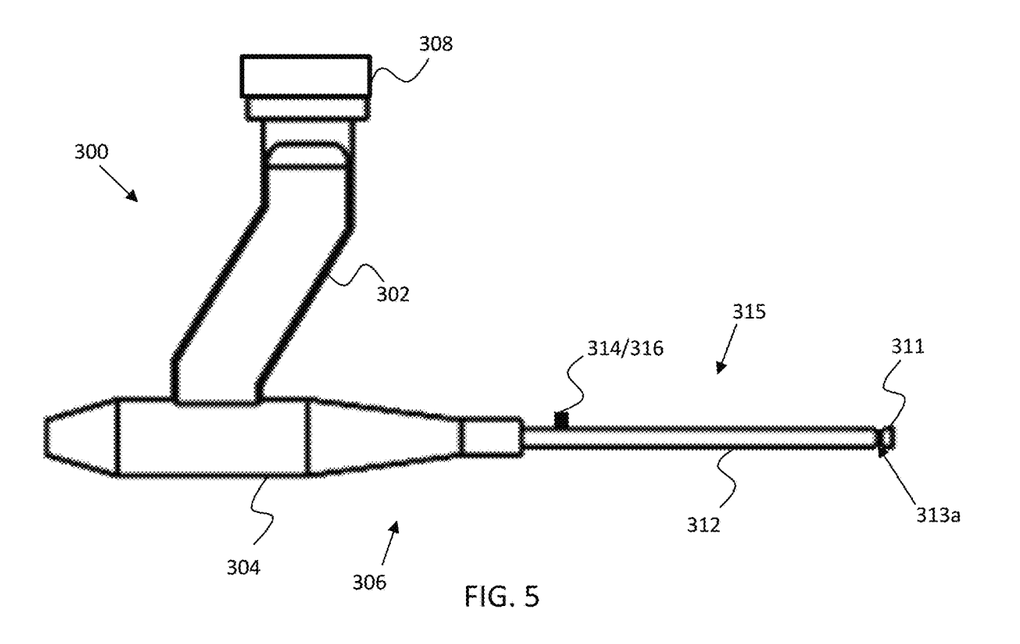
FIG. 5 is a schematic view showing an exemplary end-effector assembly having a cutting tool comprising a novel debris detection system comprising a light source and a receiver (i.e., a detector) formed in accordance with the present invention.

With reference to FIGS. 3, 4, and 5, embodiments of devices associated with the methods (100, 200) are shown. More particularly, FIG. 3 shows an end-effector assembly 300 comprising an extension arm 302, a housing 304, and a cutting tool 306. Extension arm 302 extends from the housing 304 and is configured to attach the end-effector assembly 300 to a distal flange 308 (or coupler) of a robotic system (i.e., a computer-assisted and/or robotic surgical cutting system). The housing 304 may house a motor or other actuator to rotationally drive a cutter 310 of the cutting tool 306. The cutter 310 may include a shaft having one end connected with the motor or actuator, and a cutting end 311 at the opposing end of the shaft. The cutting end 311 may illustratively be an end-mill, drill bit, or other cutting device capable of removing bone. The cutting tool 306 further includes a sleeve 312 that extends from the housing 304 to surround and support the shaft of the cutter 310. Irrigation tubing 313 may further connect to the end-effector assembly 300 to supply irrigation fluid to the surgical site. The irrigation tubing 313 may be connected to a fluid source and pump, where fluid is pumped through the irrigation tubing 313 and then out of one or more ports on the end-effector assembly 300 (e.g., a port 313a located at the distal end of sleeve 312 adjacent to cutting end 311).

Assembled on a longitudinal axis of the cutting tool 306 (e.g., on the sleeve 312 of cutting tool 306) is a novel debris detection system 315 comprising a light source 314 and a receiver 316. It should be appreciated that light source 314 and receiver 316 can be attached or assembled (i.e., mounted) to any part of a cutting tool (e.g., handle, housing, casing, or built into the sleeve or within a housing) or cutting system so long as the light source and receiver can perform the functions described herein.

In particular embodiments, light source 314 is located on a proximal portion of the cutting tool 306 and the receiver 316 is positioned at a distal portion of the cutting tool 306. In such a configuration, as shown in FIG. 4, light emitted from the light source 314 will travel through any surgical debris D located between the light source 314 and the receiver 316 while the cutting tool 305 is cutting bone B. Therefore, the intensity of the light detected by the receiver 316 is a direct indication of the presence and/or an amount of surgical debris D at the surgical site (i.e., a lower intensity of received light equates to more debris being present at the surgical site). In response to the presence or the amount of surgical debris D, the cutting system may adjust at least one of (i) the amount of irrigation supplied to the surgical site, (ii) a feed rate of the cutting tool 306, (iii) a direction of the cutting tool 306, (iv) a spindle speed of the cutting tool 306, and/or (v) a combination thereof. By way of example but not limitation, if the amount of surgical debris D reaches a threshold amount, any one or more of the following adjustments may be made: the irrigation supply is increased; the feed rate of the cutting tool 306 is temporarily reduced; the direction of the cutting tool 306 is temporarily reversed; and/or the spindle speed of cutter 310 is temporarily reduced. The temporary adjustment may allow the surgical site to be properly irrigated or cleaned prior to resuming normal operating parameters.

To permit the cutting system to make the adjustment(s) discussed above, novel debris detection system 315 (i.e., the light source 314 and receiver 316) is coupled to at least one of a processor, a controller, or a computing system in order to communicate with the computer-assisted and/or robotic surgical cutting system. The coupling between the novel debris detection system 315 and the computer-assisted and/ or robotic surgical cutting system may be made via a wired or wireless connection.

In some embodiments of the present invention, the light source 314 on the cutting tool 306 includes additional hardware components. By way of example but not limitation, such additional hardware components may include: a light driving element; a microprocessor to process data to/from the cutting system; a power source (e.g., a battery); a wireless transmitter to transmit data to/from the cutting system or receiver; software (embedded or otherwise provided); or any combination thereof. Similarly, the receiver 316 on the cutting tool 306 may include additional hardware components. By way of example but not limitation, such additional hardware components may include: a microprocessor to process the light received from the light source 314 and any other data to/from the cutting system; a power source (e.g., a battery); a wireless transmitter to transmit data to/from the cutting system or light source; embedded software; or any combination thereof.

It should also be appreciated that prior to cutting, the surgical site may contain a particular fluid (e.g., a gas or saline), whereas during cutting the surgical site may contain a different fluid, e.g., a slurry of surgical debris comprised of blood, bone chips and irrigation fluid. And it should be appreciated that a specific wavelength of light (or a range of wavelengths of light) emitted by the light source 314 may have its/their wavelength(s) modified by passage through a fluid prior to reaching the receiver 316. How the wavelength (s) of light change when passing through a particular fluid present at the surgical site may provide an indication of the nature of the fluid present at the surgical site, e.g., changes in the wavelength(s) of light passing through a fluid present at the surgical site may provide an indication of the amount (and/or type) of surgical debris present at the surgical site. Thus, in another form of the invention, changes in the wavelength(s) of light emitted by the light source 314 and received by the receiver 316 may be used to determine the presence and/or amount of surgical debris present at the surgical site. Stated another way, if the wavelength of the light emitted by light source 314 is changed by interaction with fluid before the light is detected by receiver 316, the variation in the wavelength of the light may be used to determine the presence and/or amount of surgical debris present at the surgical site.

With reference to FIG. 5, there is shown another embodiment of a novel debris detection system 315 which may be used together with a computer-assisted and/or robotic surgical cutting system according to the methods (100, 200) discussed above. The end-effector assembly 300 comprises the aforementioned novel debris detection system 315, except that with the embodiment shown in FIG. 5, the light source 314 and receiver 316 of novel debris detection system 315 are both positioned at a proximal portion of the shaft of the cutting tool 306. It will be appreciated that, in some embodiments of the present invention, the light source 314 and receiver 316 of novel debris detection system 315 are bundled together as a single unit, while in alternative forms the light source 314 and receiver 316 of novel debris detection system 315 are spaced apart from one another and/or may comprise separate units. In this form of the invention, light emitted from the light source 314 is reflected off of any surgical debris at the surgical site before reaching the receiver 316. By way of example but not limitation, the reflected light may be analyzed in order to be correlated to the amount of surgical debris present at the surgical site by the following method. First, a specific wavelength of light or a range of wavelengths of light may be used to discern one fluid from another fluid present at the surgical site. How the wavelength(s) of light reflect(s) or absorb(s) when striking a particular fluid present at the surgical site may provide an indication of the amount (and/or type) of surgical debris present at the surgical site. By way of example but not limitation, if the surgical site contains a slurry of surgical debris comprised of blood, bone chips, and irrigation fluid, light of (a) selected wavelength(s) will reflect off, or be absorbed by, the slurry of surgical debris in a different manner than where the surgical site contains only irrigation fluid (e.g., the light coming off a slurry of surgical debris may have higher or lower intensities, or different wavelengths, etc., than the light coming off irrigation fluid alone). Thus, by knowing the intensity and/or wavelength(s) of light directed at the surgical site and analyzing the intensity and/or wavelength(s) of light reflected off the surgical site, the amount (and/or type) of surgical debris present at the surgical site may be determined and the aforementioned adjustments to computer-assisted and/or robotic surgical the cutting system may be made to improve cutting performance.

In a particular embodiment, sound or pressure waves may be transmitted through the irrigation fluid to break up the surgical debris. The sound or pressure waves may be created with a controlled vibrating object or pump (not shown) in communication with the irrigation fluid to create the sound or pressure waves in the irrigation fluid. Upon the detection of the presence and/or an amount of surgical debris, one or more processors or computing systems may cause the vibrating object or pump to generate the sound or pressure waves in the irrigation fluid. The sound or pressure propagates through the irrigation fluid to the surgical site to break up the surgical debris.

Figure 6:
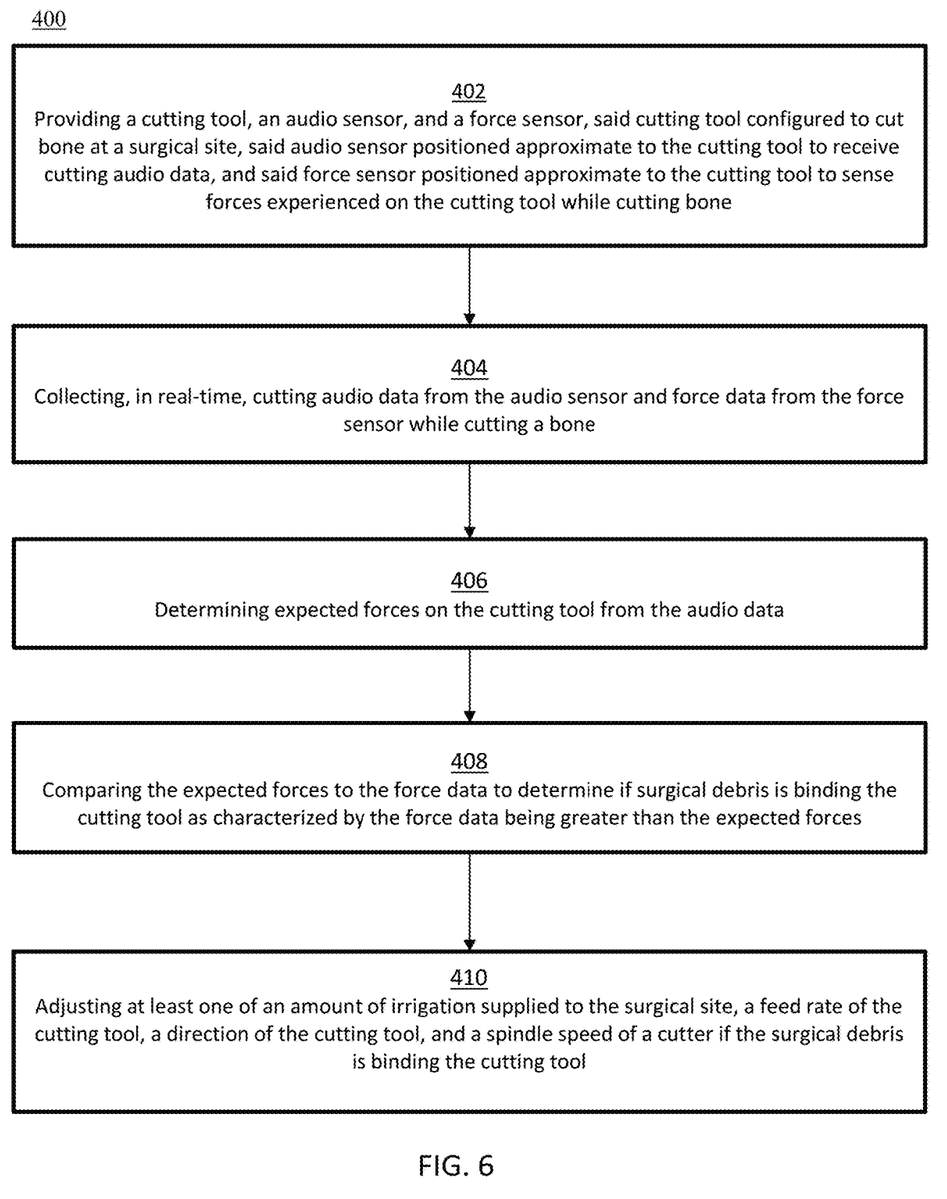
FIG. 6 is a flow diagram showing a novel method for detecting the presence and/or amount of surgical debris present at a surgical site during cutting using audio data to improve the performance of a cutting system.

Method of Detecting Surgical Debris with Audio Data to Improve Cutting Performance With reference FIG. 6, there is shown a flow diagram of a novel method 400 for detecting surgical debris at a surgical site utilizing audio data, the data obtained from which may be used to improve the cutting performance of a cutting system. More particularly, the method 400 includes the following steps. A cutting tool, an audio sensor, and a force sensor is provided. The cutting tool is configured to cut bone at a surgical site, the audio sensor is positioned proximate to the cutting tool to receive cutting audio data, and the force sensor is positioned proximate to the cutting tool to sense the forces experienced on the cutting tool while cutting bone [block 402]. During cutting, cutting audio data is collected from the audio sensor and force data is collected from the force sensor, both in real-time [block 404]. Expected forces experienced on the cutting tool are determined from the audio data [block 406], as will hereinafter be discussed. The expected forces and the force data are compared against one another in order to determine if surgical debris is binding the cutting tool as might be expected where the force data from the force sensor is greater than the expected force data [block 408]. If it is determined that surgical debris is binding the cutter 310, the cutting system adjusts at least one of (i) the amount of irrigation supplied to the surgical site, (ii) the feed rate of the cutting tool 306, (iii) the direction of the cutting tool 306, and (iv) the spindle speed of the cutter 310.

Specific embodiments of the aforementioned method 400 and the devices and system associated therewith are further described below.

Figure 7:
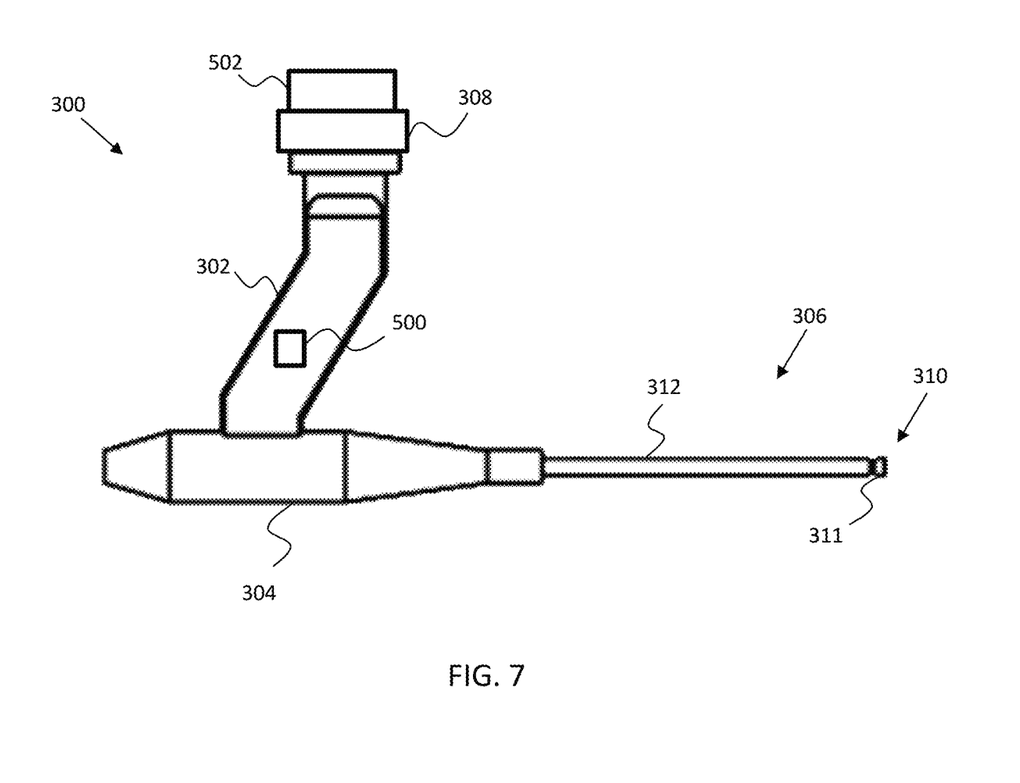
FIG. 7 is a schematic view showing an end-effector assembly comprising an audio sensor which forms part of a novel debris detection system formed in accordance with the present invention.
Figure 8:
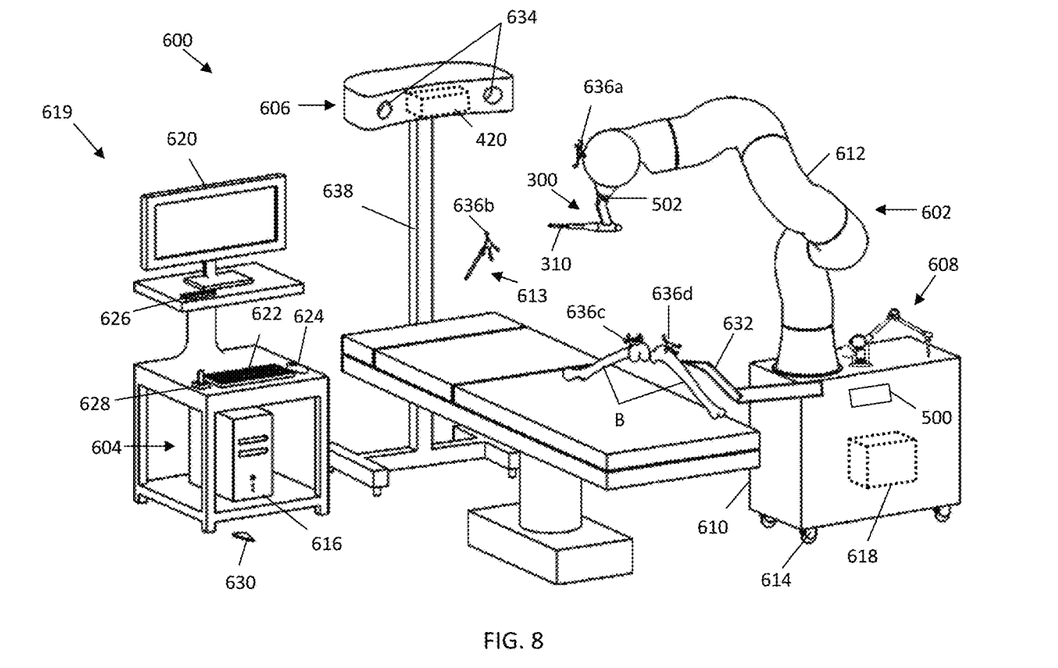
FIG. 8 is a schematic view showing a novel robotic surgical system comprising a novel debris detection system formed in accordance with the present invention which is capable of detecting surgical debris present at a surgical site so as to improve the cutting performance of the robotic system.

More particularly, in this form of the invention, an audio sensor 500 (e.g., a microphone) in communication with a computer is present in the operating room "OR" (e.g., located on the end-effector assembly 300 as shown in FIG. 7, on the robot as shown in FIG. 8, or elsewhere in the operating room) so as to collect audio data from noise emitted by the cutter 310 during cutting. Audio data can be correlated to the spindle speed of the cutter 310, and may further be correlated to the spindle speed of the cutter 310 cutting of particular types of bone B. By way of example but not limitation, a particular audio frequency may be correlated with a particular spindle speed, and/or a particular spindle speed when cutting a particular type of bone B (e.g., trabecular bone, cortical bone, bone comprising densities between trabecular bone and cortical bone, etc.). And because the noise emitted by the cutter 310 (i.e., the audio data) is generated due to the contact forces between the cutter 310 and the bone B, a mathematical model, correlation, or look-up table may be generated and used to correlate the audio frequencies with force data using empirical data. By way of example but not limitation, the empirical data used to generate such a mathematical model, correlation, or look-up table (i.e., to correlate audio frequencies with force data) may be generated in advance by cutting cadaver bones with the cutter 310 for a variety of different surgical plans. While cutting the cadaver bones, acoustic data and force data are collected using the aforementioned audio sensor 500 (e.g., a microphone) and the aforementioned force sensor (e.g., force sensor 502, FIG. 8), respectively. The acoustic data, force data, and the cutting parameters (e.g., spindle speed, feed rate, etc.) are then used to build the mathematical model, correlation, or look-up table to correlate these variables, thus providing a relationship between the audio data and the expected forces between the cutter 310 and the bone B. In the operating room, while cutting the patient's actual bone, the model, correlation, or look-up table may be used to determine the expected forces correlating to the collected audio data.

Audio data and force data are preferably collected simultaneously. Looking now at FIG. 8, the force data may be collected by a force sensor 502 (e.g., a 6-DOF force sensor of the sort known in the art). The force sensor 502 may be positioned proximal to the cutting tool 306 (FIG. 3) in order to detect the forces experienced by the cutting tool 306. The expected forces to be experienced by cutting tool 306, as determined from the acoustic data received by audio sensor 500 (FIG. 7), are then compared to the actual force data received by the force sensor 502. Under normal operating conditions, the expected forces (as determined based on the acoustic data received by the audio sensor 500) and the force data (received from the force sensor 502) are within statistical agreement. If the force data is indicative of forces experienced by the cutting tool 306 being greater than the expected forces (e.g., statistically higher or above a specified threshold), then there is a strong possibility that surgical debris is binding, impinging, or otherwise applying an additional force against the cutting tool 306. This is because the audio data provides the expected forces occurring between the cutting end 311 and the bone B, whereas the force sensor 502 is sensing all the forces against the cutting tool 306. Therefore, if the force data is higher than the expected forces, the surgical debris may be causing the additional forces against the cutting tool 310. If it is determined that the surgical debris is binding the cutter 310, the cutting system adjusts at least one of (i) the amount of irrigation supplied to the surgical site, (ii) the feed rate of the cutting tool 306, (iii) the direction of the cutting tool 306, and (iv) the spindle speed of the cutter 310, as described above.

In a particular embodiment, sound or pressure waves may be transmitted through the irrigation fluid to break up the surgical debris. The sound or pressure waves may be created with a controlled vibrating object or pump (not shown) in communication with the irrigation fluid to create the sound or pressure waves in the irrigation fluid. Upon the detection of the presence and/or an amount of surgical debris, one or more processors or computing systems may cause the vibrating object or pump to generate the sound or pressure waves in the irrigation fluid. The sound or pressure propagates through the irrigation fluid to the surgical site to break up the surgical debris.

Robotic Surgical System

With reference to FIG. 8, an embodiment of a robotic surgical system 600 is shown capable of implementing embodiments of the inventive method described above. The aforementioned devices and methods are particularly useful for a robotic surgical system 600, which traditionally experiences longer surgical times compared to manual techniques or techniques using hand-held tracked instrumentation.

The surgical system 600 generally comprises a surgical robot 602, a computing system 604, and a tracking system 606 and/or a mechanical digitizer arm 608.

The surgical robot 602 may include a movable base 610, a manipulator arm 612 connected to the base 610, an end-effector assembly 300 located at a distal end of the manipulator arm 612, and a force sensor 502 positioned proximal to the end-effector assembly 300 for sensing forces experienced by the end-effector assembly 300. The base 610 includes a set of wheels 614 to maneuver the base 610, which may be fixed into position using a braking mechanism such as a hydraulic brake. The base 610 may further include an actuator to adjust the height of the manipulator arm 612. The manipulator arm 612 includes various joints and links to manipulate the end-effector assembly 300 in various degrees of freedom. The joints are, illustratively, prismatic, revolute, spherical, or a combination thereof. In some embodiments, the surgical system 600 includes at least one of a tracked hand-held digitizer 613, or a mechanical digitizer arm 608 attached to the base 610. The tracked digitizer 613 may include a tracking array 636b to be tracked by the tracking system 606, while the digitizer arm 608 may have its own tracking computer or may be directly connected with a device computer 618 (i.e., the device computer for surgical robot 602).

The computing system 604 may generally comprise a planning computer 616; the device computer 618; a tracking computer 619 if a tracking system 606 is present; and peripheral devices (see below). The planning computer 616, device computer 618, and tracking computer 619 may be separate entities, one-in-the-same, or combinations thereof, depending on the surgical system. Furthermore, in some embodiments, a combination of the planning computer 616, the device computer 618, and/or tracking computer 619 are connected to one another via a wired or wireless communication. The peripheral devices (see above) allow a user to interface with the surgical system components and may include: one or more user-interfaces, such as a display monitor 620 for a graphical user interface (GUI); and user-input mechanisms, such as a keyboard 622, mouse 624, pendent 626, joystick 628, foot pedal 630, or the display monitor 620 in some embodiments has touchscreen capabilities.

The planning computer 616 contains hardware (e.g., processors, controllers, memory, etc.), software, data and utilities that are, in some forms of the present invention, dedicated to the planning of a surgical procedure, either pre-operatively or intra-operatively. By way of example but not limitation, this may include reading medical imaging data, segmenting imaging data, constructing three-dimensional (3D) virtual models, storing computer-aided design (CAD) files, providing various functions or widgets to aid a user in planning the surgical procedure, and generating surgical plan data. By way of example but not limitation, the final surgical plan may include pre-operative bone data, patient data, registration data including the position and orientation (POSE) of the points P defined relative to the pre-operative bone data, implant position data, trajectory parameters, and/or operational data. By way of example but not limitation, the operational data may include: a set of instructions for modifying a volume of tissue that is defined relative to the anatomy, such as a set of cutting parameters (e.g., cut paths, spindle-speeds, feed-rates, etc.) in a cut-file to autonomously modify the volume of bone; a set of virtual boundaries defined to haptically constrain a tool within the defined boundaries to modify the bone; or a set of planes or drill holes to drill pins in the bone. In one form of the invention, the operational data specifically includes a cut-file for execution by a surgical robot to automatically modify the volume of bone, which is advantageous from an accuracy and usability perspective. The surgical plan data provided by the planning computer 616 may be transferred to the device computer 618 and/or tracking computer 619 through a wired or wireless connection in the operating room (OR); or transferred via a non-transient data storage medium (e.g., a compact disc (CD), a portable universal serial bus (USB) drive) if the planning computer 616 is located outside the OR. In one form of the invention, the surgical plan is transferred via visible light communication such as is described in U.S. Pat. App. Pub. No. 2017/0245945, which patent application is hereby incorporated herein by reference.

The device computer 618 in some inventive embodiments is housed in the moveable base 610 and contains hardware, software, data and utilities that are preferably dedicated to the operation of the surgical robot 602. This may include surgical device control, robotic manipulator control, the processing of kinematic and inverse kinematic data, the execution of registration algorithms, the execution of calibration routines, the execution of operational data (e.g., cut-files, trajectory parameters, etc.), coordinate transformation processing, providing workflow instructions to a user (e.g., a surgeon), and utilizing position and orientation (POSE) data from the tracking system 606. The device computer 618 may further be in communication with the light source 314, receiver 316, force sensor 502, audio sensor 500, or a plurality of strain gauges 632 attached to the bone, to compute at least one of: an intensity of light on the receiver 316, an adjustment parameter (e.g., feed rate, spindle speed, etc.) based on the detected presence or amount of surgical debris, expected forces from the audio data, the comparison of the expected forces and the force data from the force sensor, and other computational or processing steps to perform the aforementioned methods (100, 200, 400). In addition, the device computer 618 may be in communication with a display monitor 620 to display data related to the various embodiments of the methods (100, 200, and 400) described above.

The tracking system 606 may be an optical tracking system that includes two or more optical receivers 634 to detect the position of fiducial markers (e.g., retroreflective spheres, active light emitting diodes (LEDs), etc.) uniquely arranged on rigid bodies. The fiducial markers arranged on a rigid body are collectively referred to as a tracking array (636a, 636b, 636c, 636d), where each tracking array 636 has a unique arrangement of fiducial markers, or a unique transmitting wavelength/frequency if the markers are active LEDs. The fiducial markers may likewise be integrated or attached with a device directly to act as a tracking array for that device. An example of an optical tracking system is described in U.S. Pat. No. 6,061,644, which patent is hereby incorporated herein by reference. The tracking system 606 may be built into a surgical light, located on a boom attached to a stand 638, or built into the walls or ceilings of the operating room (OR). The tracking computer 619 may include tracking hardware, software, data and utilities to determine the position and orientation (POSE) of objects (e.g., bones B, surgical robot 602) in a local or global coordinate frame. The position and orientation (POSE) of the objects is collectively referred to herein as "POSE data", where this POSE data may be communicated to the device computer 618 through a wired or wireless connection. Alternatively, the device computer 618 may determine the POSE data using the position of the fiducial markers detected from the optical receivers 634 directly.

The POSE data is determined using the position data detected from the optical receivers 634 and operations/processes such as image processing, image filtering, triangulation algorithms, geometric relationship processing, registration algorithms, calibration algorithms, and coordinate transformation processing.

The POSE data is used by the computing system 604 during the procedure to update the position and orientation (POSE) and/or coordinate transforms of the bone B, the surgical plan, and the surgical robot 602 as the manipulator arm 612 and/or bone B move during the procedure, such that the surgical robot 602 can accurately execute the surgical plan. Data from the tracking system 606 may also be used to determine at least one of the bone motion vectors and/or bone motion magnitudes as described above. In one form of the invention, the tracking system 606 is in communication with the display monitor 620 (which displays the aforementioned indication mechanisms) to provide instructions to display the aforementioned indications as they relate to the various embodiments of the methods (100, 200, and 400) described above.

In another form of the invention, the robotic surgical system 600 does not include an optical tracking system 606, but instead utilizes a bone fixation and bone monitoring system (e.g., strain gauges 632) that fix the bone directly to the surgical robot 602 to monitor bone movement as described in U.S. Pat. No. 5,086,401, which patent is hereby incorporated herein by reference. It should also be appreciated that other tracking systems may be used in addition to, or in lieu of, an optical tracking system 606, including a mechanical tracking system and an electromagnetic tracking system.

Other Embodiments

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the described embodiments in any way. Rather, the foregoing detailed description will provide those skilled in the art with a convenient roadmap for implementing the exemplary embodiment or exemplary embodiments. It should be understood that various changes may be made in the function and arrangement of elements without departing from the scope as set forth in the appended claims and the legal equivalents thereof.

The invention claimed is:

1. A system for detecting debris at a surgical site, the system comprising:
    a cutting tool configured to cut bone; and
    a debris detection system comprising:
        a light source mounted proximal to the surgical site for emitting light;
        a receiver mounted to the cutting tool for receiving light emitted from the light source, wherein the light emitted from the light source passes through debris present at the surgical site before the light is received by the receiver; and
        a processor configured to determine a presence and/or amount of debris present at a surgical site using a change in a characteristic of light emitted by the light source and received by the receiver.

2. The system according to claim 1 wherein the processor is configured to determine the presence and/or amount of debris present at the surgical site using a change in intensity of the light received by the receiver.

3. The system according to claim 2 wherein the processor is configured to use a look-up table to determine the presence and/or amount of debris present at the surgical site by looking up, in the look-up table, the change in the intensity of light received by the receiver.

4. The system according to claim 1 wherein the processor is configured to determine the presence and/or amount of debris present at the surgical site using a change in wavelength of the light received by the receiver.

5. The system according to claim 4 wherein the processor is configured to use a look-up table to determine the presence and/or amount of debris present at the surgical site by looking up, in the look-up table, the change in the wavelength of the light received by the receiver.

6. The system of claim 1 further comprising a controller for varying, based on the presence and/or amount of debris present at the surgical site, at least one of (i) an amount of irrigation supplied to the surgical site, (ii) a feed rate of the cutting tool, (iii) a direction of the cutting tool, and (iv) a spindle speed of a cutter associated with the cutting tool.

7. The system of claim 1 wherein the cutting tool comprises a cutter supported by a sleeve, wherein the receiver is mounted to the sleeve of the cutting tool.

8. A system for detecting debris at a surgical site, the system comprising:
    a cutting tool configured to cut bone; and
    a debris detection system comprising:
        a light source mounted proximal to the surgical site for emitting light;
        a receiver mounted proximal to the surgical site for receiving light emitted from the light source, wherein the light source is mounted proximal to the surgical site and the receiver is mounted proximal to the surgical site such that light emitted by the light source is reflected off of surgical debris present at the surgical site before the light is received by the receiver; and
        a processor configured to determine a presence and/or amount of debris present at a surgical site using a change in a characteristic of light emitted by the light source and received by the receiver.

9. The system according to claim 8 wherein the processor is configured to determine the presence and/or amount of debris present at the surgical site using a change in intensity of the light received by the receiver.

10. The system according to claim 9 wherein the processor is configured to use a look-up table to determine the presence and/or amount of debris present at the surgical site by looking up, in the look-up table, the change in the intensity of light received by the receiver.

11. The system according to claim 9 wherein the processor is configured to determine the presence and/or amount of debris present at the surgical site using a change in wavelength of the light received by the receiver.

12. The system according to claim 11 wherein the processor is configured to use a look-up table to determine the presence and/or amount of debris present at the surgical site by looking up, in the look-up table, the change in the wavelength of the light received by the receiver.

13. The system of claim 8 further comprising a controller for varying, based on the presence and/or amount of debris present at the surgical site, at least one of (i) an amount of irrigation supplied to the surgical site, (ii) a feed rate of the cutting tool, (iii) a direction of the cutting tool, and (iv) a spindle speed of a cutter associated with the cutting tool.

14. A system for detecting debris at a surgical site, the system comprising:
    a cutting tool configured to cut bone; and
    a debris detection system comprising:
        a light source mounted to the cutting tool for emitting light;
        a receiver mounted proximal to the surgical site for receiving light emitted from the light source, wherein the light emitted from the light source passes through debris present at the surgical site before the light is received by the receiver; and
        a processor configured to determine a presence and/or amount of debris present at a surgical site using a change in a characteristic of light emitted by the light source and received by the receiver.

15. The system according to claim 14 wherein the processor is configured to determine the presence and/or amount of debris present at the surgical site using a change in intensity of the light received by the receiver.

16. The system according to claim 15 wherein the processor is configured to use a look-up table to determine the presence and/or amount of debris present at the surgical site by looking up, in the look-up table, the change in the intensity of light received by the receiver.

17. The system according to claim 14 wherein the processor is configured to determine the presence and/or amount of debris present at the surgical site using a change in wavelength of the light received by the receiver.

18. The system according to claim 17 wherein the processor is configured to use a look-up table to determine the presence and/or amount of debris present at the surgical site by looking up, in the look-up table, the change in the wavelength of the light received by the receiver.

19. The system of claim 14 further comprising a controller for varying, based on the presence and/or amount of debris present at the surgical site, at least one of (i) an amount of irrigation supplied to the surgical site, (ii) a feed rate of the cutting tool, (iii) a direction of the cutting tool, and (iv) a spindle speed of a cutter associated with the cutting tool.

20. The system of claim 14 wherein the cutting tool comprises a cutter supported by a sleeve, wherein the light source is mounted to the sleeve of the cutting tool.

\* \* \* \* \*